US008834383B2

(12) United States Patent
Muehlsteff et al.

(10) Patent No.: US 8,834,383 B2
(45) Date of Patent: Sep. 16, 2014

(54) APPARATUS TO MONITOR PULSATING OBJECTS WITHIN THE BODY

(75) Inventors: Jens Muehlsteff, Aachen (DE); Jeroen Adrianus Johannes Thijs, Aachen (DE); Robert Pinter, Germany (DE)

(73) Assignee: Koninklijke Philips N.V., Eindhoven (NL)

( * ) Notice: Subject to any disclaimer, the term of this patent is extended or adjusted under 35 U.S.C. 154(b) by 1111 days.

(21) Appl. No.: 12/438,747

(22) PCT Filed: Aug. 28, 2007

(86) PCT No.: PCT/IB2007/053449
§ 371 (c)(1),
(2), (4) Date: Feb. 25, 2009

(87) PCT Pub. No.: WO2008/026157
PCT Pub. Date: Mar. 6, 2008

(65) Prior Publication Data
US 2010/0069745 A1    Mar. 18, 2010

(30) Foreign Application Priority Data

Aug. 30, 2006 (EP) .................................. 06119803

(51) Int. Cl.
| A61B 5/02 | (2006.01) |
| A61B 5/11 | (2006.01) |
| A61B 5/024 | (2006.01) |
| A61B 5/05 | (2006.01) |
| G01S 13/88 | (2006.01) |
| A61B 5/00 | (2006.01) |
| G01S 13/62 | (2006.01) |

(52) U.S. Cl.
CPC ............... *A61B 5/02438* (2013.01); *A61B 5/11* (2013.01); *G01S 13/88* (2013.01); *A61B 5/02405* (2013.01); *A61B 5/0507* (2013.01); *A61B 5/6823* (2013.01); *A61B 5/1107* (2013.01); *G01S 13/62* (2013.01); *A61B 5/7239* (2013.01)
USPC .......................................... 600/500; 600/501

(58) Field of Classification Search
None
See application file for complete search history.

(56) References Cited

U.S. PATENT DOCUMENTS

| 3,483,860 | A | 12/1969 | Namerow |
| 3,993,995 | A | 11/1976 | Kaplan et al. |
| 4,638,808 | A | 1/1987 | Mawhinney |
| 4,967,751 | A | 11/1990 | Sterzer |
| 2008/0269589 | A1* | 10/2008 | Thijs et al. ................. 600/407 |

FOREIGN PATENT DOCUMENTS

| DE | 2539870 B1 | 9/1976 |
| JP | 2004085293 A | 3/2004 |
| JP | 2005237569 A | 9/2005 |
| JP | 2006510880 A | 3/2006 |
| WO | 0116554 A2 | 3/2001 |
| WO | WO2007010460 A2 | 1/2007 |

OTHER PUBLICATIONS

Thijs et al., A Comparison of Continuous Wave Doppler Radar to Impedance Cardiography for Analysis of Mechanical Heart Activity, 2005, Proceedings of the 2005 IEEE Engineering in Medicine and Biology 27th Annual Conference, pp. 3482-3485.*
Thijs et al: "A Comparison of Continuous Wave Doppler Radar to Impedance Cardiography for Analysis of Mechanical Heart Activity" Engineering in Medicine and Biology Society, 2005. IEEE-EMBS 2005. 27th Annual International Conference of the Shanghai, China Sept. 1-4, 2005, Piscataway, NJ, USA,IEEE, 2005, pp. 3482-3485, XP031001290 ISBN: 0-7803-8741-4.
Papp M A et al: "Doppler Microwave. A Clinical Assessment of Its Efficacy as an Arterial Pulse Sensing Technique" Investigative Radiology, Philadelphia, PA, US, vol. 22, No. 7, Jul. 1987, pp. 569-573, XP009078552.
Muehlsteff J et al: "The use of a two channel Doppler radar sensor for the characterization of heart motion phases" Engineering in Medicine and Biology Society, 2006. EMBS '06. 28th Annual International Conference of the IEEE, IEEE, PI, Aug. 2006, pp. 547-550, XP031186419 ISBN: 1-4244-0032-5.
Infineon Technologies; Microwave Motion Sensor, KMY 24, Apr. 1, 1999, www.datasheetcatalog.com.
Michahelles, F. et al., "Less Contact: Heart-Rate Detection without even Touching the User", IEEE Wearable Computers, 2004. ISWC 2004. Eighth International Symposium, Oct.-Nov. 2004 http://www.vision.ethz.ch/publ/iswc04_radar.pdff.
E.H. Haselhoff et al., "A Dedicated System for Cardia MRI: Gyroscan Intera CV", Medica Mundi 44/2 Nov. 2000, pp. 2-9.
Lohninger, G., "Doppler Module KMY 24: Radar Sensor Detects Motion and Direction", Applications Sensors, Components XXXI (19996) No. 4, pp. 30-31.
Moore, S.K., "Unhooking Medicine [wireless network]", Detecting heartbeat with a cell phone, Spectrum, IEEE, vol. 38, Issue: 1, Jan. 2001 http://ieeexplore.ieee.org/iel5/6/19336/00901156.pdff.
Matthews, M. et al., "A Non-Contact Vital Signs Monitor", Critical Reviews in Biomedical Engineering, 2000, v. 28 n. 1-2, p. 173-178 http://www.begellhouse.com/journals/4b27cbfc562e21b8,63fe0825280eb6c4,0cb32ca2742042d8.htmll.

* cited by examiner

Primary Examiner — Benjamin P Blumel
(74) Attorney, Agent, or Firm — Michael W. Haas

(57) ABSTRACT

The invention concerns an apparatus, system, wearable apparatus and concomitant processing system to detect instants in time at which a cyclically pulsating object within the body of an individual is temporarily quiescent, such an object being the heart, an artery or the lungs. The essence of the invention is the use of a doppler radar motion sensor, normally used for vehicular speed detection or the detection of building occupancy. The doppler radar motion sensor is arranged to transmit electromagnetic signal towards the object and receive reflected electromagnetic signal from the object, and the apparatus is further arranged to identify the instants in time at which the reflected signal indicates the object is temporarily quiescent. The invention is particularly suitable for ambulatory monitoring of the heart.

15 Claims, 3 Drawing Sheets

APPARATUS TO MONITOR PULSATING OBJECTS WITHIN THE BODY

FIELD OF THE INVENTION

The invention concerns an apparatus to detect instants in time at which a cyclically pulsating object within the body of an individual is temporarily quiescent.

BACKGROUND OF THE INVENTION

Detection of instants at which the heart is quiescent, in other words, temporarily still within the normal cardiac cycle, is known within medical imaging and allows the presentation of acquired diagnostic data which is corrected for heart movement. In particular, 'Application Guide, GYROSCAN NT VOLUME 2: Scan Methods', section 5.9, Coronary Artery Imaging, describes the use of a trigger delay to capture images of the heart at a relatively quiet moment. 'Magnetic Resonance Imaging, Physical Principles and Sequence Design', by E. Mark Haacke, et al., Wiley-Liss, ISBN 0-471-35128-8, section 24.4.1, describes triggering data acquisition to the cardiac cycle. Together, these discloses indicate how techniques of magnetic resonance imaging in combination with ECG gating can be exploited to identify the instants in time at which the beating human heart is quiescent within the normal cycle of pulsation.

U.S. Pat. No. 3,483,860 discloses the use of doppler radar to measure the activity of the heart and in particular discloses that the output doppler signal can be subjected to mathematical differentiation to provide a signal representing the blood ejection rate.

Magnetic resonance imaging is expensive and the image data takes considerable time to acquire. Therefore magnetic resonance imaging is not suitable for regular monitoring of heart activity and in particular is not suitable for ambulatory monitoring. In addition it is not suitable for measurement of the quiescent periods of any other pulsating object in the body, for example an artery, because the reliance on ECG gating ties the application of this imaging technique to the heart.

SUMMARY OF THE INVENTION

It is an object of the invention to provide an alternative method for identifying the instants of time at which a pulsating object within the body is quiescent. This is achieved according to the invention whereby the apparatus comprises a doppler radar motion sensor arranged to transmit electromagnetic signal towards the object and receive reflected electromagnetic signal from the object, and in which the apparatus is further arranged to identify the instants in time at which the reflected signal indicates the object is not moving.

Doppler radar motion sensors are used to detect the speed and direction of motion of vehicles in roadside speed detection cameras and are also used to detect motion of occupants within buildings. In the latter case they are incorporated into what are known as 'intruder alarms', also commonly known as 'burglar detectors'. In operation, the motion detector transmits an electromagnetic signal and detects return signals reflected back from objects in the path of the electromagnetic beam. The electromagnetic waves in this transmitted beam undergo a frequency shift upon reflection by an object moving with a component of motion along the direction of travel of the beam and this shift is detectable in the reflected signal.

In both the measurement of vehicle speed and the measurement of vehicle direction of motion, and also in the detection of room occupancy based on the detection of occupant movement, the doppler radar sensor detector receives reflected electromagnetic signals from a large, physically translating object, with general size of an order of magnitude of meters. In the case of vehicle motion detection this object is commonly a car, van, lorry or other vehicle. In the case of detection of a building occupant, the object is a moving person, normally of the order of a meter or more high. Further, in all these cases the object detected by the doppler radar motion sensor is physically, laterally moving in the sense that it is translating its overall mass laterally from one position to another. The doppler radar motion sensor is designed to register this gross, lateral movement.

Surprisingly it has been found that a doppler radar motion sensor is suitable for measuring the motion of pulsating objects in the human body, where those objects have themselves a size of the order of magnitude of centimeters and the amplitude of the pulsation is of the order of a centimeter or so, or as low as millimeters. The pulsating objects which can be detected do not move laterally in the sense of translating their overall mass from one position to another, but stay in one place and pulsate. Examples of objects in the body which undergo this form of motion are the heart and, separately, the arteries, and in addition the lungs. In all cases there is no overall translation of the object but instead some steady rhythmic motion of the overall object. The object itself retains its general position within the body.

Further, it was surprisingly found that although pulsating objects do not translate their position laterally, the signal from the doppler radar motion sensor is sufficient to detect instants within the cycle of pulsation at which the object is temporarily not pulsating.

Thus a doppler radar motion sensor can be used to detect cyclical motion within the body and to further detect when that cyclical motion ceases, albeit temporarily.

Equipment to perform the method is easier to use than the equipment associated with magnetic resonance imaging and requires simple placement of the doppler radar motion sensor against the body, for example the chest when used to detect activity of the heart. The equipment is also compact enough to be placed against an arm or leg, for example, for the detection of activity of arteries. It is particularly suitable for simple measurement of heart activity as the equipment can be worn in a comfortable sling or harness around the chest and, correspondingly, it is suitable for the simple detection of the time instants at which the heart is quiescent. Identification of such instants allows the calculation of physiologically relevant periods in the heart cycle, such as calculation of the length of the atrial phase and the ventricular phase, as is known in the art. Because the invention can be performed using simple and small equipment it is also more suited to repeated measurements, for example in patient monitoring. The invention can therefore be used for long term monitoring of the lengths of relevant physiological phases in a patient's heart. For example, repeated use on a daily or weekly basis of the invention would allow indication of any lengthening over time, for example, of the ventricular phase of a patient's heart, and thus be a useful adjunct to existing methods of heart monitoring.

The invention also relates to a system to detect instants in time at which a cyclically pulsating object within the body of an individual is temporarily quiescent, comprising a doppler radar motion sensor arranged to transmit electromagnetic signal towards the object and receive reflected electromagnetic signal from the object, the doppler radar motion sensor arranged to transmit information representative of this received signal to a processor, and the processor arranged to receive the transmitted signal and identify the instants in time at which the reflected signal indicates the object is temporarily quiescent.

This system has the advantage that it allows the method of the invention to be performed, in particular over multiple devices and thereby provide maximum flexibility in assessing the internal motion of pulsating objects in the body of an individual. The doppler radar motion sensor and processor can be coupled to each other in any known way and this includes for example coupling via a physical connection, such as a wire or bus, or coupling wirelessly.

This system can be applied to the monitoring of the heart activity, or the activity of arteries or the activity of the lungs, or indeed any other pulsatile object inside the body.

The invention also relates to a wearable apparatus to monitor heart activity of an individual, comprising a doppler radar motion sensor arranged to transmit electromagnetic signal towards the heart of the individual and receive reflected electromagnetic signal from the heart, the doppler radar motion sensor coupled to a processor, and the processor arranged to transmit signal information representative of the received reflected electromagnetic signal, the transmitted signal information to be received by a processing system, which processing system is arranged to identify the instants in time at which the reflected signal indicates the object is temporarily quiescent. Transmitting includes any known form of transmission including wireless transmission by any known means, transmission using telecommunications or telephone lines and transmission along a fixed connection, for example a wire.

This apparatus has the advantage, in the case where transmission is wireless or uses telecommunications or transmission along a telephone line, that it can be worn by an individual while they move around and can therefore acquire signals allowing monitoring of heart activity while the individual is ambulatory. It has the further advantage that the wearable apparatus need only comprise a suitable doppler radar motion sensor for the production of electromagnetic signals and need not comprise the processing system which identifies the instants in time. This processing system may be remote from the wearable apparatus, thereby saving space and weight in the wearable apparatus. Thus the wearable apparatus has the advantage that it provides output signals to a remote processing system which performs the calculation of the instants of time. The remote processor may be physically located in the same room as the individual, may be located in another room in the same building or even in another building.

The wearable apparatus can be worn by the individual on a strap or a harness or using other carrying means. Because the electromagnetic signals can penetrate through cloth and other wearable materials the apparatus can also be carried in a pocket constructed on the clothing of the individual and arranged to be situated in a position where an optimal signal is detected by the sensor.

The invention also relates to a processing system, for receiving the signal information transmitted from a wearable apparatus to monitor heart activity of an individual, the wearable apparatus comprising a doppler radar motion sensor, the processing system arranged to receive signal information representative of the electromagnetic signal reflected from the heart of an individual, and the processing system arranged to identify the instants in time at which the reflected signal indicates the heart is temporarily quiescent.

This processing system has the advantage that it processes the signals from a portable apparatus arranged to detect doppler radar signals from within the chest of an individual and processes them to produce signals representative of the quiescent instants according to the invention.

Thus the wearable apparatus in combination with the remote processor together offer a solution which solves the problem of how to arrange for ambulatory monitoring of heart activity of the individual which can also identify the time instants at which the heart is temporarily quiescent.

The invention also has the further advantage that it can be used to provide monitoring of heart activity using a world wide web service. In this case, the individual who is monitored wears the sensor in a housing, arranged in some way on his or her person, as above, so that suitable signals are detected which have been reflected from the heart, and the processor which calculates the instants in time at which the heart is quiescent is contactable via the world wide web. In this case the skilled person can arrange for the signal from the wearable apparatus to be transmitted to an intermediate processor, a computer with a connection to the world wide web, say, which is arranged to transmit the signal representative of the detected signals through the world wide web to the remote processor. Alternatively, the wearable apparatus can be equipped with suitable processing to allow for the direct transmission of the signal representative of the detected signals into the world wide web to the remote processor.

Thus the system solves the problem of how to provide monitoring of heart activity from a location remote from the location of the individual being monitored.

The apparatus of the invention is particularly advantageously arranged when it emits continuous wave electromagnetic waves, although as a feature this is not necessary. The apparatus of the invention achieves the desired result if the emitted and reflected signals are of such a duration that they are able to encode information from at least a single heart beat. This can be achieved if the electromagnetic signals are emitted in the form of a continuous beam. However, pulsed electromagnetic signals can also be used if each single pulse is long enough to encode the information from a single heart beat, or, for example, if the time interval between pulses is very short in comparison with the time it takes the heart to beat once. In the latter case, each pulse encodes some fraction of the information available in each heart beat about the heart activity. In the case where a train of very short pulses with a very short time interval are used the information encoded in the doppler shifted reflected signals represents a sampling of information from the heart.

The apparatus of the invention can be used with a two channel doppler radar motion sensor arranged to produce electromagnetic signals of frequency in a range of between 400 MHz and 5 GHz. This range is found to be particularly advantageous for producing signals which are reflected from the heart. However, the apparatus works in a particularly advantageous manner when the frequency is in a range of between 800 MHz and 4 GHz.

The apparatus is operated advantageously when it emits electromagnetic signals which are of a single frequency, within the limits of conventional operation of electromagnetic antenna, as will be appreciated by the person skilled in the art.

In a particularly advantageous embodiment of the invention, a doppler radar motion sensor is used which mixes the signal from the shifted, reflected electromagnetic wave with the original emitted signal in two mixer diodes. The mixer diodes are driven by the same oscillator, but with a defined phase difference. The result is two output voltage signals which allow detection of the direction of motion of the reflecting object, either towards or away from the doppler radar motion sensor. In this way the doppler radar motion sensor is able to detect when the reflecting object is moving towards or away from the detector, and so in this embodiment of the invention the apparatus detects the time instants at which the reflected signal indicates that the reflecting object is neither moving towards nor away from the doppler radar motion detector.

The polarity of the phase shift between these two signals is dependent on whether the target is moving towards the doppler radar motion detector or away from the doppler radar motion sensor. If the object is moving towards the doppler radar motion sensor then the phase shift is negative and when the object is moving away from the doppler radar motion detector the phase shift between the two signals is positive. It was found that for this particular doppler radar motion sensor, there is a cross over point between the period of time when the reflected signal from a reflecting object indicates that the reflected object is moving towards the doppler radar motion detector and the period of time when the reflected signal indicates that the object is moving away from the doppler radar motion sensor. This cross over point occurs when there is no phase difference between the two signals. Surprisingly, it was found that this cross over point could be used to indicate the instants in time when a pulsating object in the body is temporarily quiescent. Thus in a particularly advantageous embodiment, instants of time when the object is quiescent are identified as the instants in time when the phase difference, or phase shift, between these two signals is substantially zero. By substantially zero is meant zero within the normal tolerances of signal measurement and processing, as appreciated by the skilled person.

It was found that a particularly advantageous technique to detect the instants of time when the phase difference between the two signals was zero was to detect the instants of time when both signals contemporaneously reach the same maximum or same minimum amplitude. Further, it was found that a particularly advantageous technique to achieve this was to detect the instants in time when the first order derivatives of both signals are simultaneously substantially zero. By substantially zero is meant zero within the normal tolerances of signal measurement and processing, as appreciated by the skilled person.

The invention is further elucidated and embodiments of the invention are explained using the following figures.

BRIEF DESCRIPTION OF THE DRAWINGS

As is commonly known, the heart is the organ which pumps blood around the body. It is subdivided into 4 chambers, consisting of 2 atria, which receive blood entering the heart, with deoxygenated blood returning from the body entering into the right atrium and oxygenated blood from the lungs entering into the left atrium, and 2 larger ventricles which are responsible for pumping blood out of the heart. The right ventricle pumps deoxygenated blood received from the right atrium out of the heart and to the lungs, where it is oxygenated. The left ventricle, the largest chamber in the heart, is responsible for pumping oxygenated blood received from the left atrium out into the rest of the body. As is also known, measurements from electrocardiography, ECG, show that the heart pumps in a cyclical fashion and ECG measurements allow identification of certain phases common to the electrical sequence of the heart. FIG. 1 shows a typical output trace from an ECG measurement. The characteristic spikes shown in a typical trace are labeled P, Q, R, S and T, as indicated. It is known that the P spike, or wave, is representative of the depolarization, or excitation, of the atria. The QRS spikes, known commonly as the QRS-complex, are representative of the excitation of the ventricles. The QRS-complex masks any signal from the repolarization of the atria. The T spike, or T wave, is representative of the repolarization of the ventricles.

Figure 1:
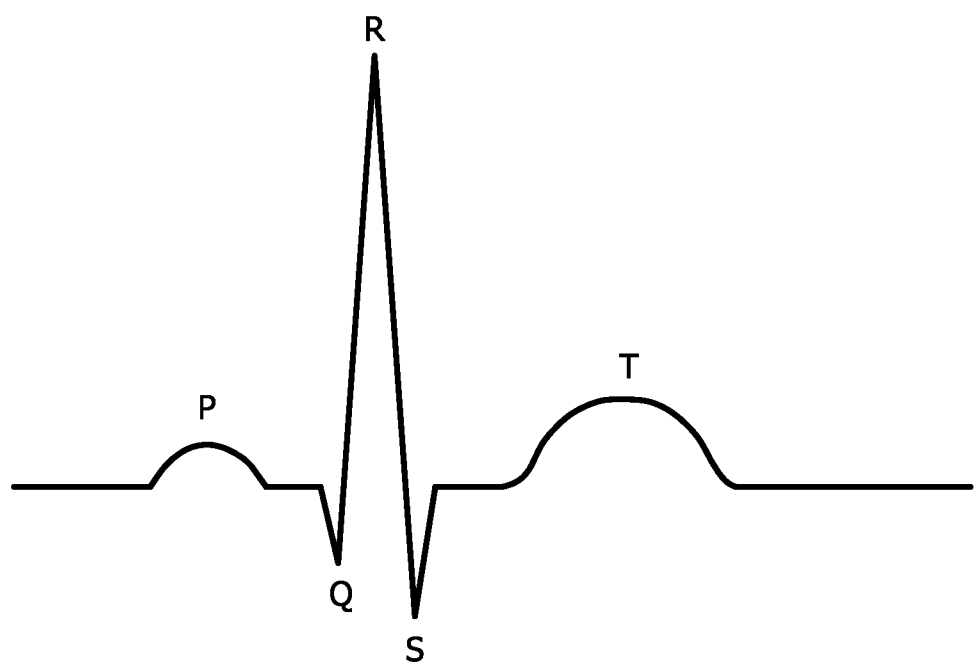
FIG. 1 shows a typical trace from an ECG measurement of the heart.

Doppler radar motion sensors for the detection of doppler shifted signals are commercially available, and are used for the purposes of detection of movement using the far field of the beam, for example in the measurement of vehicular speed or of movement of occupants within a room. It is now found, according to the invention that not only can such motion detectors be used for near field measurements, and are in fact surprisingly suitable for detecting mechanical heart activity via the detection of doppler shifted signals from the heart, they can also be used to identify the instants in time when the heart is quiescent, in other words temporarily still within the normal cardiac cycle.

Generally in such doppler radar motion sensors, as is known in the art, an antenna emits an electromagnetic wave which, when it is reflected from the surfaces of an object moving with a component of velocity non-transverse to the impinging electromagnetic wave, produces a shift in the frequency of the electromagnetic wave reflected back to the antenna. This shift in frequency is called the doppler shift. This doppler shifted reflected wave is detected by an antenna in the motion detector, which may or may not be the same antenna as the emitting antenna. The relative speed of movement of the reflecting object is encoded in the frequency shift of the detected reflected wave and this value can be extracted using known techniques. The change in frequency experienced by an electromagnetic signal reflected from either the heart, or a tissue boundary oscillating at substantially the same frequency as the heart, for example an artery wall, is about 1 Hz, and in this case greater accuracy of measurement is achieved if the phase change in the signal is measured.

A sensor advantageously used in the apparatus of the invention contains a 2.45 GHz oscillator operating in continuous mode. It is known that electromagnetic radiation is strongly absorbed in human tissue at around the frequencies of 2 to 10 GHz, but it is found, according to this highly advantageous embodiment of the invention, that the radiation produced from an antenna operating at 2.45 GHz, although absorbed and scattered to some extent by layers of tissue, produces a detectable signal.

A particularly advantageous embodiment utilizes a commercially available Microwave Motion Sensor KMY 24 unit, a two channel motion detector made by Micro Systems Engineering GmbH. It contains a 2.45 GHz oscillator and receiver in the same housing and works in continuous wave mode. The dimensions of the beam are, amongst other things, dependent on the dimensions of the antenna and in this case the unit contains an optimized patch antenna with minimized dimensions and a width of 3.5 cm, producing a beam with a near field radius of around 2 cm. This provides a workable compromise between too large an antenna, which would produce a wide beam easily contaminatable by reflections from other structures, and too small an antenna, which would produce a narrow beam which is difficult to position satisfactorily. In practice, a beam with a width in the range of 1 cm to 2.5 cm is advantageous because it provides a workable compromise between the two extremes described above. A beam with a width in the range of 1.5 cm to 3 cm is particularly advantageous for application of the apparatus to large adults or adults with an enlarged heart. A beam with a width in the range of 0.5 cm to 1.75 cm is advantageous for application of the apparatus to small children.

Figure 2:
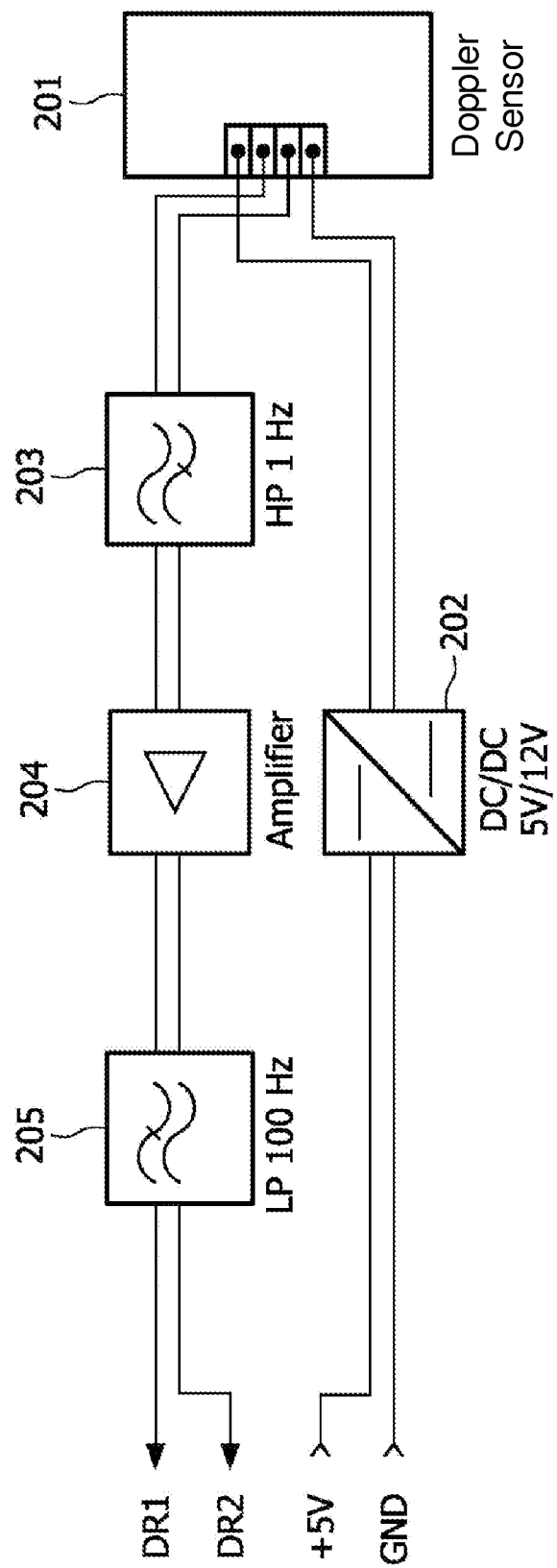
FIG. 2 shows a block diagram of the apparatus of the invention.

The commercially available unit is utilized in the following way. FIG. 2 shows a block diagram of the apparatus. The doppler radar motion sensor 201 is powered by a voltage supply 202. Doppler radar motion sensor 201 may include one or more of a detector, a transducer, and/or other components. The output of sensor 201 is processed through a high pass filter 203, a preamplifier 204 and a low pass filter 205. It was found experimentally that the high pass filter 203 should comprise a capacitance of 100 nF and a resistor of 1 M$\Omega$, as this enabled a faster decay of the signal while removing the DC part of the signal from the doppler module. The time constant $\tau$ of 0.1 s produces a cut-off frequency of 1.59 Hz. Although the signal being detected is reflected from the heart which beats with a frequency of the order of 1 Hz, the attenuation of this first order high pass filter is low enough not to destroy the signal. The gain of the preamplifier 204 can be set in a range of 1 to 1000 but it was found that a particularly advantageous gain was 500. To enable sampling, an $8^{th}$ order low pass filter was realized with a cutoff frequency of 100 Hz using operational amplifiers.

FIG. 2 also shows two output signals, DR1 and DR2, from the doppler sensor, the phase difference between which is measured to provide additional information about the direction of movement of the reflecting object.

It was found that the whole assembly is sensitive enough to process signals that are reflected by the heart.

Experimental results show that the positioning of the sensor relative to the heart is important in detecting a useful signal. The electromagnetic signals must be reflected from the heart itself in order for mechanical heart information to be encoded in the reflected signals. However, it is found experimentally that individual variation between subjects alters the correct position or positions of the sensor in respect of optimal signal detection for each individual. However, if both the detected and output signals are visually displayed on a display screen it is possible to see if the sensor is correctly placed. If the sensor is placed in such a way that the heart is not in the emitted beam of signals, or is not reflecting the emitted signals back to the receiver, little or no cyclical activity will be seen in the reflected beam. If the sensor is well positioned a cyclical signal will be seen. A certain amount of experimentation is required in the correct positioning of the sensor on the surface of the chest of the individual before a suitable signal and therefore the correct position identified. It has been found that arranging the sensor so that the emitted beam impinges on a plane structure predominantly parallel to the plane of the sensor, for example a section of heart wall muscle, is highly advantageous in receiving an adequate reflected signal.

The sensor can be incorporated in a suitable housing which is advantageously dimensioned so that it can be arranged flat against the chest, for example the sternum of the individual. Suitable dimensions are between 3 and 6 cm wide and between 4 and 7 cm long. These sizes allow for the hardware to be contained in the housing while maintaining the housing at a size which can be used effectively on an individual.

The technical steps to be performed in the processing of the acquired data to provide the instants in time can be undertaken by the person skilled in the art once he is aware that it is these points in the output signal which are sought. In particular, in the specific embodiment when there are two output signals with a relative phase change, for example in the KMY24 unit, the identification of the instants in time when there is no phase change between both signals can easily be achieved using known techniques of signal processing.

Figure 3:
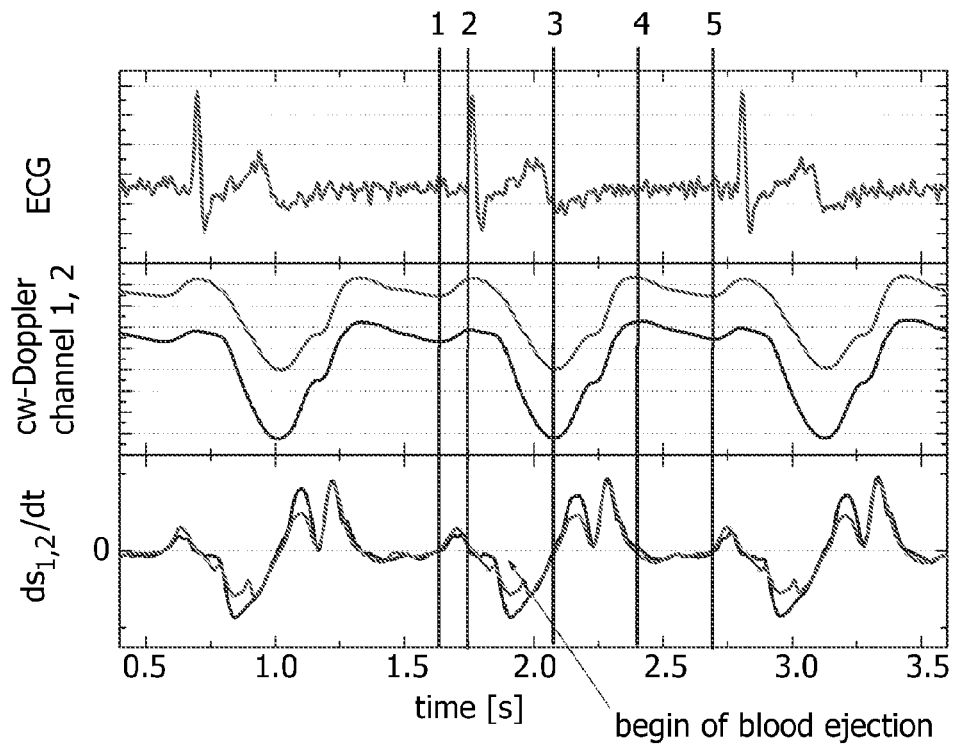
FIG. 3 shows the results of a measurement acquired with the doppler radar motion detector positioned at the sternum, a plot of the first order time derivative of the output and a plot of the signal from a standard 1 lead ECG.

FIG. 3 shows the results of the measurement combination with the Doppler radar motion sensor positioned at the sternum and a standard 1 lead ECG is shown. The plot from the 1 lead ECG is shown at the top. The middle diagram shows the radar measurements from the two channels. The lower part of the diagram shows the time derivative of both radar signals. It can be seen that there are several points per heart beat period for which both time derivatives have a simultaneous zero-crossing. These points are indicated by the numbers 1 to 5. It can be seen, by examination of FIG. 3 that point 5 lies at the same point of the cardiac cycle as point 1 thus it can be clearly seen that the invention, when applied to heart monitoring, allows identification of 4 specific points in the cardiac cycle. These zero-crossings indicate the point in time where the heart movement has a point of zero velocity, due to a change of direction or a pause in the movement. These points can be used to separate the different phases of the heart's pumping function:

1. Atrial phase: From point 1 to point 2, the contraction of the atrium produces small velocity changes in both channels.
2. Contraction phase: Point 2 to point 3 defines the phase in which the ventricle contraction takes place. This is also reflected in the large velocity changes in this phase.
3. Point 3 to point 5 shows the filling phase where velocities decrease and the atria are filling again, the point 4 cannot be interpreted by a feature in the ECG.

Although there are several zero crossings in the time derivative of a single channel, only a limited number of points show a zero crossing in both derivatives simultaneously. Thus it is shown that the embodiment of the two channel doppler radar motion sensor is particularly advantageous for detecting the instants in time at which the heart is temporarily quiescent.

Figure 4:
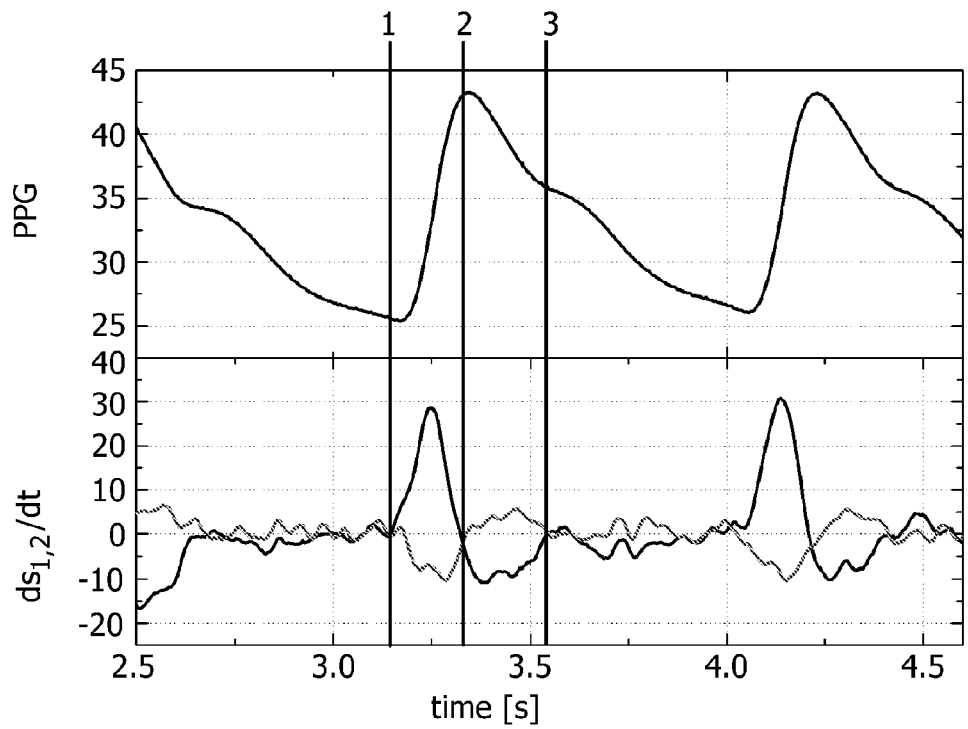
FIG. 4 shows the time derivatives of the measured signals from the doppler radar motion detector reflected from an artery in the leg and synchronized with a finger photo-plethysmogram as reference.

FIG. 4 shows the time derivatives of the measured Doppler signals synchronized with a finger photo-plethysmogram as reference, for the signals from a two channel Doppler radar sensor positioned to receive reflected electromagnetic waves from the right leg artery of a 33-year-old male. Both Doppler radar signal derivatives have common zero-crossings at indicated points 1, 2, and 3 and these indicate states of no movement in the artery. These states of no movement in the artery also represent states of no movement in the heart cycle, as the heart is positioned upstream of the artery and dictates the motion of the arterial walls by its rhythmic ejection of blood. These states of no movement also coincide with the characteristic points of the PPG, as known to the skilled person in the art of plethysmography. The small time difference is due to the different propagation times to the leg and finger. The Doppler radar technique together with the presented signal analysis is therefore a promising approach to evaluate the dilatation and constriction of arteries or the comfortable extraction of pulse transit times.

The invention claimed is:
1. An apparatus configured to detect instants in time at which a cyclically pulsating object within the body of an individual is temporarily quiescent, the apparatus comprising:
 a doppler radar motion sensor (201), the sensor configured to transmit an electromagnetic signal toward the object and receive a reflected electromagnetic signal from the object; and a processing system configured to identify the instants in time at which the reflected signal indicates the object is temporarily quiescent.

2. The apparatus of claim 1, wherein the apparatus is configured to detect a direction of motion of a moving object toward and/or away from the detector, the processing system further configured to identify the instants in time at which the reflected signal indicates the object is neither moving toward nor away from the detector.

3. The apparatus of claim 2, wherein the doppler radar motion sensor (201) is arranged to output two further signals, wherein a phase shift between the two further signals is non-zero when the object is moving toward and/or away from the detector, the processing system further configured to identify the instants in time at which there is substantially no phase shift between the two further signals.

4. The apparatus of claim 3, wherein the processing system is arranged to identify the instants in time at which the two further signals attain their maximum amplitudes or minimum amplitudes contemporaneously.

5. Apparatus as claimed in claim 3, characterized in that the apparatus is arranged to identify the time instants for which the first order derivative of both further signals are simultaneously substantially zero.

6. The apparatus of claim 1, wherein the doppler radar motion sensor (201) is configured to emit a continuous wave electromagnetic signal.

7. The apparatus of claim 6, wherein the doppler radar motion sensor (201) emits the continuous wave electromagnetic signal at a frequency in a range between 400 MHz and 5 GHz.

8. The apparatus of claim 7, wherein the doppler radar motion sensor (201) emits the continuous wave electromagnetic signal at a frequency in a range between 800 MHz and 4 GHz.

9. The apparatus of claim 8, wherein the doppler radar motion sensor (201) emits the continuous wave electromagnetic signal at a frequency of 2.45 GHz.

10. A method to detect instants in time at which a cyclically pulsating object within the body of an individual is temporarily quiescent, the method comprising transmitting doppler radar from a doppler radar motion sensor (201) toward the object, receiving reflected radar from the object, and identifying, with a processing system, the instants in time at which the reflected signal indicates the object is not moving.

11. A system configured to detect instants in time at which a cyclically pulsating object within the body of an individual is temporarily quiescent, the system comprising:
a doppler radar motion sensor (201), the sensor configured to:
transmit an electromagnetic signal toward the object; and
receive reflected electromagnetic signal from the object; and
a processor configured to:
transmit information representative of the received signal to a processing system, the processing system configured to,
receive the transmitted signal and
identify the instants in time at which the reflected signal indicates the object is temporarily quiescent.

12. A wearable apparatus configured to monitor heart activity of an individual, the apparatus comprising a doppler radar motion sensor (201), the sensor configured to transmit an electromagnetic signal toward the heart of the individual and receive a reflected electromagnetic signal from the heart, the sensor (201) coupled to a processor, the processor configured to transmit signal information representative of the received reflected electromagnetic signal, the transmitted signal information received by a processing system, the processing system configured to identify the instants in time at which the reflected signal indicates the object is temporarily quiescent.

13. A processing system configured to receive signal information transmitted from a wearable apparatus, the wearable apparatus configured to monitor heart activity of an individual, the wearable apparatus comprising a doppler radar motion sensor, the processing system configured to receive signal information representative of an electromagnetic signal reflected from the heart of the individual, the processing system configured to identify the instants in time at which the reflected signal indicates the heart is temporarily quiescent.

14. The system of claim 13, wherein the system is further configured to provide an indication of the identified instants in time at which the heart is quiescent.

15. The system of claim 13, wherein the system is further configured to trigger the capture of one or more images of the heart at the identified instants in time at which the heart is quiescent.

* * * * *